United States Patent
Takemoto et al.

[11] Patent Number: 5,432,262
[45] Date of Patent: Jul. 11, 1995

[54] METHOD OF PURIFYING α-L-ASPARTYL-L-PHENYLALANINE METHYL ESTER

[75] Inventors: Tadashi Takemoto, Kawasaki; Katsumi Sugiyama, Yokkaichi, both of Japan

[73] Assignee: Ajinomoto Co., Inc., Tokyo, Japan

[21] Appl. No.: 3,297

[22] Filed: Jan. 12, 1993

[30] Foreign Application Priority Data

Jan. 14, 1992 [JP] Japan .................. 4-004890

[51] Int. Cl.$^6$ .............. A61K 37/02; C07K 1/00; C07K 5/06; C07C 101/32
[52] U.S. Cl. .................. 530/344; 530/801; 560/40; 560/41; 562/445; 562/571
[58] Field of Search .......... 562/401, 402, 450, 571, 562/445; 530/801, 344; 560/41, 40; 514/19

[56] References Cited

U.S. PATENT DOCUMENTS

| | | |
|---|---|---|
| 4,309,341 | 1/1982 | Kubo et al. |
| 4,634,790 | 1/1987 | Shinohara et al. ............ 560/40 |
| 4,780,561 | 10/1988 | Mita et al. ................ 560/40 |
| 4,897,507 | 1/1990 | Takahashi et al. ........... 560/41 |

FOREIGN PATENT DOCUMENTS

| | | |
|---|---|---|
| 0256515 | 2/1988 | European Pat. Off. |
| 0399605 | 11/1990 | European Pat. Off. |
| 0484769 | 5/1992 | European Pat. Off. |
| 0514939 | 11/1992 | European Pat. Off. |
| 0514940 | 11/1992 | European Pat. Off. |
| 5140071 | of 1976 | Japan. |

*Primary Examiner*—Robert J. Hill, Jr.
*Assistant Examiner*—A. M. Davenport
*Attorney, Agent, or Firm*—Oblon, Spivak, McClelland, Maier, & Neustadt

[57] ABSTRACT

Mixture containing α-L-aspartyl-L-phenylalanine methyl ester and 3-benzyl-6-carboxymethyl-2,5-dioxopiperazine are brought into contact with hydrochloric acid in an aqueous solvent to precipitate α-L-aspartyl-L-phenylalanine methyl ester hydrochloride and 3-benzyl-6-carboxymethyl-2,5-dioxopiperazine, which are then separated from each other by classification.

5 Claims, 1 Drawing Sheet

METHOD OF PURIFYING α-L-ASPARTYL-L-PHENYLALANINE METHYL ESTER

BACKGROUND OF THE INVENTION

1. Field of the Invention

This invention relates to a method of purifying α-L-aspartyl-L-phenylalanine methyl ester (hereinafter abbreviated as α-APM) from mixtures containing, as impurities, at least 3-benzyl-6-carboxymethyl-2,5-dioxopiperazine (hereinafter abbreviated as DKP) by efficiently removing the impurities after precipitation with aqueous hydrochloric acid.

2. Discussion of the Background

α-APM is a peptide sweetener having a degree of sweetness about 200 times as high as that of sucrose. It is a low-calorie substance of good quality which has been in great demand in recent years. However, the compound is unstable and cyclizes easily by heating to form DKP. Accordingly, α-APM prepared by any method unavoidably contains DKP as an impurity. Obtaining pure α-APM by efficiently removing DKP has been an eternal problem faced by producers of this substance. A variety of methods have been developed to solve this problem, but each suffers from a significant drawback. Japanese Patent Publication No. 35660/1977 discloses a resin used to purify α-APM but the method involves decomposition of α-APM during the operation, and complicated operations for eluting the product and regenerating the resin. Japanese Patent Publication No. 40071/1976 discloses a method of removing DKP by crystallizing it at a pH of 2–2.7. However, because DKP forms very fine, needle crystals, which can hardly be separated continuously on an industrial scale using commonly employed equipment, such as ordinary centrifugal separators, the method is not applicable. Therefore a filter press, which has low operation efficiency, must be used. Japanese Patent Kokai No. 117445/1974 discloses an n-butanol extraction method, therefore, the solvent n-butanol has to be recovered. In addition, any of these methods require a crystallization step to recover α-APM after the operations described above, and hence two steps are essential in order to purify α-APM by removing DKP.

SUMMARY OF THE INVENTION

Accordingly, an object of this invention is to provide a novel method of purifying α-APM from a mixture containing L-aspartyl-L-phenylalanine methyl ester and at least 3-benzyl-6-carboxymethyl-2,5-dioxopiperazine which comprises contacting, in an aqueous solution, aspartyl-L-phenylalanine methyl ester and 3-benzyl-6-carboxymethyl- 2,5-dioxopiperazine with hydrochloric acid to precipitate both α-L-aspartyl-L-phenylalanine hydrochloride and 3-benzyl-6-carboxymethyl-2,5-dioxopiperazine; then separating said precipitated compounds from each other by classification.

DETAILED DESCRIPTION OF THE PREFERRED EMBODIMENTS

Figure 1:
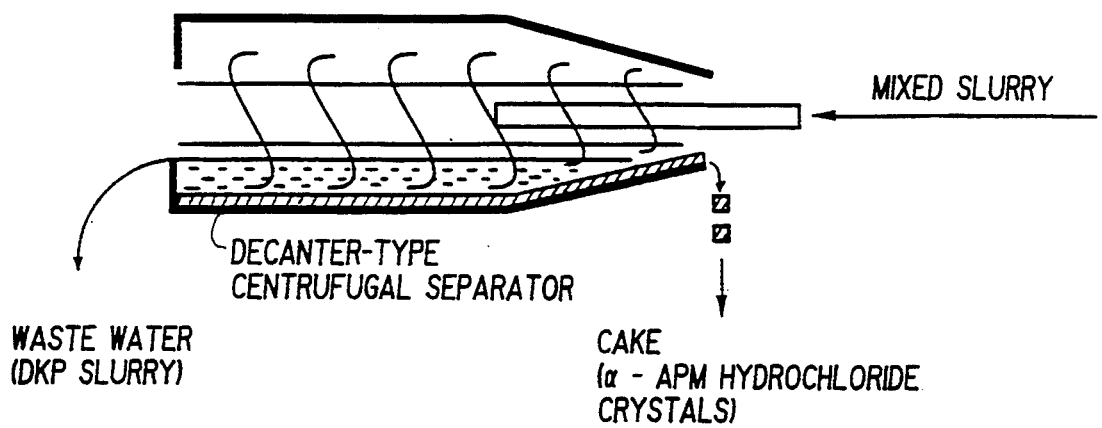
FIG. 1 is a sectional view of the decanter-type centrifugal separator.

As a result of intensive studies to solve above-mentioned problems, the present inventors found a method in which α-APM containing DKP as an impurity is brought into contact with hydrochloric acid in an aqueous solvent. α-APM hydrochloride and DKP are precipitated then separated from each other by classification, thereby removing DKP into the liquid phase. This invention was accomplished on the basis of these findings.

The present invention is applicable to the purification of α-APM containing as impurities, in addition to DKP, β-L-aspartyl-L-phenylalanine methyl ester and α-L-aspartyl-L-phenylalanine, which are impurities commonly observed in the α-APM manufacturing process, as well as L-aspartic acid, phenylalanine and derivatives thereof which are starting materials used in same manufacturing processes. All of these impurities exist in the liquid phase under the operation conditions in the methods of this invention and are therefore removed into the liquid phase efficiently.

Bringing impure α-APM containing DKP into contact with hydrochloric acid may be performed by any conventional method, but is generally performed (1) by dissolving the impure α-APM in an aqueous solvent and adding hydrochloric acid to said solution, (2) by dissolving or suspending the impure α-APM in an aqueous solvent containing hydrochloric acid, or (3) by directly adding hydrochloric acid to the solution of α-APM obtained from the reaction for preparing the same. There is no specific limitation upon the temperature of the reaction with hydrochloric acid, but a temperature in the range from 10° to 70° C. is generally preferable because an excessively high temperature can accelerate the hydrolysis of α-APM, thus lowering the yield of α-APM hydrochloride. The hydrochloric acid concentration in the reaction medium should be 0.5N or higher, but an excessively high concentration accelerates the hydrolysis of α-APM, and hence a concentration in the range from 0.5 to about 4N is generally preferable. In a preferred embodiment of methods (1) and (2) described above, the pH of the α-APM solution is first adjusted to 2–3 by addition of hydrochloric acid to crystallize DKP, thus utilizing the fact that DKP is crystallizable at a pH of 3 or less, and then adding further hydrochloric acid to adjust its concentration to a level of 0.5N or higher, thereby crystallizing α-APM hydrochloride. These methods are preferable because coagulation of DKP crystals can be avoided.

This invention is characterized in that the mixed slurry of DKP and α-APM hydrochloride obtained by the method described above is subjected to separation by classification which utilizes the difference in particle size between these two kinds of crystals, thereby giving the crystals of α-APM hydrochloride as a cake and removing the crystals of DKP into the liquid phase in the form of a slurry. Several methods of separation by classification are known. Sedimentation classification utilizes the sedimentation of particles by gravity, hydraulic classification utilizes water pressure, machine classification, and centrifugal classification utilizing centrifugal forces are also suitable. Of these, the simple centrifugal classification method is the most suitable technique. Preferable examples of machines to be used for centrifugal classification include liquid cyclones in which centrifugal force is applied by the rotation of a liquid in a fixed cylinder, and decanter-type centrifugal separators using an externally driven rotator.

As is apparent from the foregoing, the present invention ensures efficient purification of α-APM by easily removing DKP and other impurities by simple operations. Other features of the invention will become apparent in the course of the following descriptions of exemplary embodiments which are given for illustration of the invention and are not intended to be limiting thereof.

EXAMPLE 1

A mixture of 46 g α-APM and 9 g of DKP (DKP content in α-APM: 20 weight %) was suspended in 900 ml water, and this suspension was adjusted to pH 4.9 and diluted with water to a total volume of 1000 ml. The resulting suspension was heated at 50° C. until a clear solution was obtained, the pH was adjusted to 2.7 by addition of 30 ml of 35%-HCl, and the resulting solution was stirred for one hour to crystallize DKP. After cooling to 10° C., 125 ml of 35%-HCl was further added, and stirring was continued at the same temperature for four hours, giving a mixed slurry of DKP and α-APM hydrochloride. This slurry was fed into a decanter-type, centrifugal separator as shown in FIG. 1, (Model P-40OYJ; rotational speed 3600 rpm; product of Sharpless Co., Ltd.) at a speed of 20 l/hr, thus separating the slurry into a cake of α-APM hydrochloride and DKP slurry. The yield of α-APM hydrochloride cake was 99% calculated according to the formula:

yield of α-APM hydrochloride=(α-APM.HCl crystals in cake)/(α-APM.HCl crystals in slurry)

The removed rate of DKP crystals into the liquid phase was 97% calculated as: removal rate of DKP crystals=(DKP crystals in waste water)/(DKP crystals in slurry)

The amount of DKP contained in the α-APM hydrochloride crystals obtained was 0.2% based on the weight of α-APM.

EXAMPLE 2

To 100 liters of aqueous solution containing 4.6% α-APM, 0.7% DKP , 3.5% β-L-aspartyl-L-phenylalanine methyl ester, 0.4% L-aspartic acid and 0.2% L-phenylalanine, was added at 50° C., 3 liters of 35%-HCl to adjust the pH to 2.6, and the resulting mixture was stirred for one hour at the same temperature to deposit DKP crystals. This slurry was cooled to 10° C., 13 liters of hydrochloric acid was added, and the mixture was stirred for one hour at the same temperature and then for three hours at 50° C. The mixed slurry of α-APM hydrochloride and DKP thus obtained (HCl concentration: 1.5N) was fed into a decanter-type centrifugal separator (Model P-660; rotational speed 6000 rpm; product of Sharpless Co., Ltd.) at a speed of 600 l/hr, thus separating into a cake of α-APM hydrochloride and a DKP slurry (waste water). The yield of the α-APM hydrochloride crystals in the case was 100% based on the weight of the same in the feed slurry, and the removal rate of DKP crystals into the waste water was 93%. The amount of DKP contained in the cake of α-APM hydrochloride crystals was 0.5% based on the weight of α-APM, and no β-L-aspartyl-L-phenylalanine methyl ester, L-aspartic acid or L-phenylalanine was contained in the cake.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of a purifying α-L-aspartyl-L-phenylalanine methyl ester containing at least 3-benzyl-6-carboxymethyl-2,5-dioxopiperazine as impurities which comprises: contacting, in an aqueous solution, α-L-aspartyl-L-phenylalanine methyl ester containing at least 3-benzyl-6-carboxymethyl-2,5-dioxopiperazine as impurities with hydrochloric acid to precipitate α-L-aspartyl-L-phenylalanine methyl ester hydrochloride and 3-benzyl-6-carboxymethyl-2,5-dioxopiperazine; and separating said precipitated compounds from each other by classification.

2. The method as defined in claim 1, wherein 3-benzyl-6-carboxymethyl-2,5-dioxopiperazine is first precipitated by adjusting the pH to 2–3 by addition of hydrochloric acid, and then hydrochloric acid is further added to a concentration of 0.5–4N, thereby crystallizing α-L-aspartyl-L-phenylalanine methyl ester hydrochloride.

3. The method as defined in claim 1, wherein a centrifugal classifier is used to perform said separation.

4. The method as defined in claim 3, wherein said centrifugal classifier is a decanter-type centrifugal separator.

5. The method of claim 1, wherein said aqueous solution is contacted with hydrochloric acid at a temperature of from 10–70° C.

* * * * *